United States Patent

Shields et al.

[11] Patent Number: 5,816,440
[45] Date of Patent: Oct. 6, 1998

[54] OVERFOLDED STERILE GLOVE DISPENSERS

[76] Inventors: Jack W. Shields, 1950 Las Tunas Rd., Santa Barbara, Calif. 93103; W. Mark Shields, 1735 Clearview Rd., Santa Barbara, Calif. 93101

[21] Appl. No.: 813,786
[22] Filed: Mar. 1, 1997
[51] Int. Cl.⁶ .................................................. A47K 10/24
[52] U.S. Cl. ............................................. 221/45; 206/438
[58] Field of Search ................................. 221/33, 45, 46, 221/63, 48, 34; 206/438

[56] References Cited

U.S. PATENT DOCUMENTS

| | | | |
|---|---|---|---|
| 4,773,532 | 9/1988 | Stephenson | 206/438 |
| 4,951,815 | 8/1990 | Ulbrich | 206/438 |
| 4,997,105 | 3/1991 | Fischer | 221/45 |
| 5,044,494 | 9/1991 | Tamura | 206/438 |
| 5,065,863 | 11/1991 | Moyet-Ortiz | 206/438 |

FOREIGN PATENT DOCUMENTS 403602  11/1967  Austria ................................. 206/438

Primary Examiner—Kenneth Noland

[57] ABSTRACT

Containers for sterile gloves having long cuffs folding over the palms, leaving the fingers exposed beyond, are disclosed such that, upon opening, only the crease of each long cuff/palm overfold can be manually grasped. In one preferred embodiment, sterile containers initially covered with removable film are designed with single openings covered by slit film to dispense multiple surgical or examination gloves. Inside the containers, the overfolded cuffs of successive gloves are folded under the flexed fingers of the first and every succeeding glove, such that the user can serially extract externally sterile gloves by grasping the crease of each long cuff/palm overfold. One bare hand grasps the crease to glove the other. Then, the ungloved hand grasps the crease of the next glove, such that the fingers of the gloved hand can be inserted under the cuff/palm overfold to glove the bare hand. As results, the external surfaces of each extracted glove are never touched by a bare finger or any other contaminated object before use on a patient. Such containers can dispense specified numbers of examination or surgical gloves. In another embodiment, multiple pairs of surgical or examination gloves, each pair with thumbs apposed toward the palms, can be dispensed with the palms touching in separate sterile envelopes, each of which unseals to expose only the creases of the cuff overfolds. Such sterile envelopes can be boxed separately or in rolls from which each package is easily separated.

3 Claims, 3 Drawing Sheets

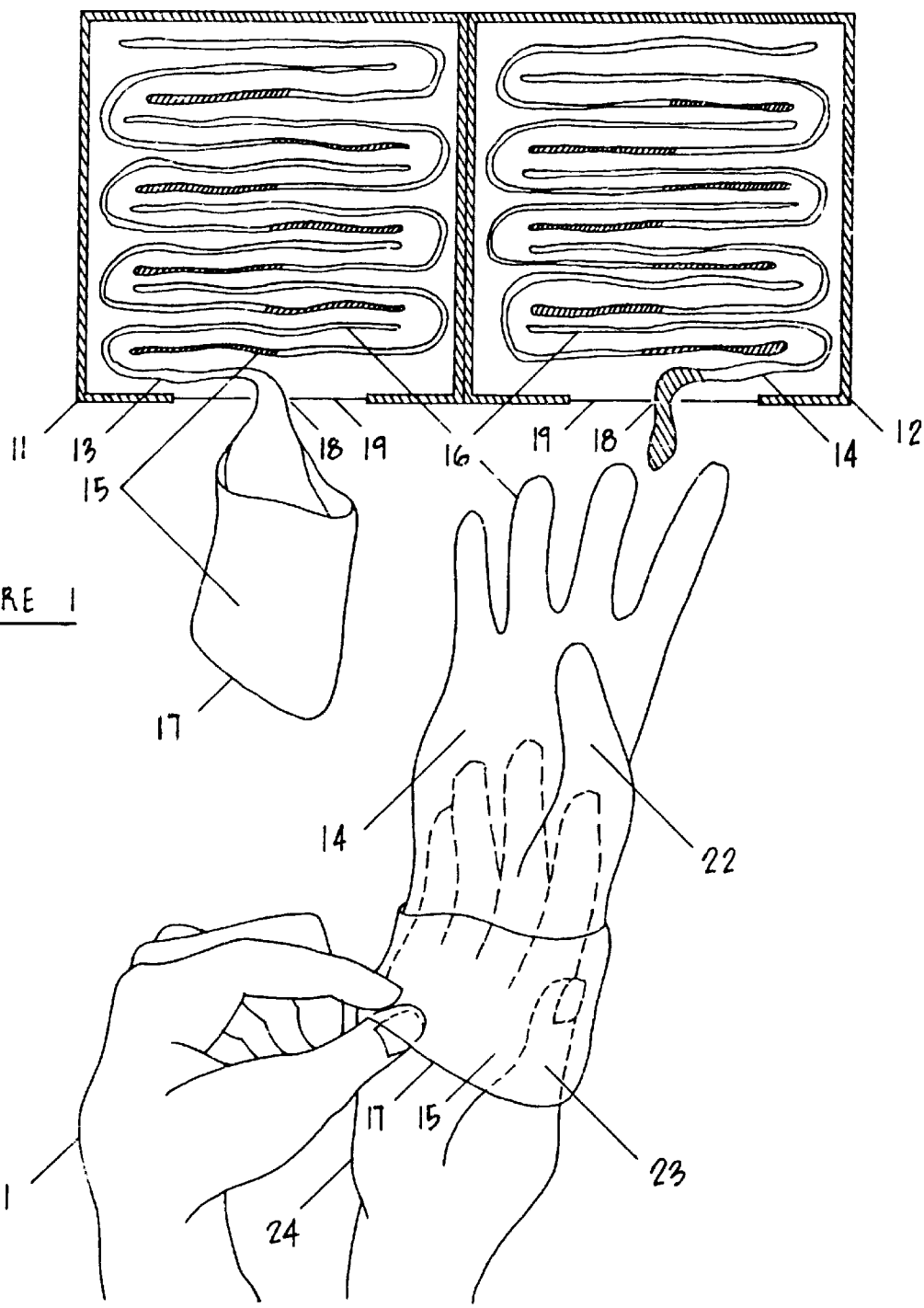

OVERFOLDED STERILE GLOVE DISPENSERS

BACKGROUND OF THE INVENTION

1. Field of Invention

The external contamination of latex or synthetic gloves employed for common procedures performed in health care settings is hazardous to patients. Contamination of the external glove surfaces with common skin-borne microorganisns, such as staphylococci or streptococci, or blood-borne microorganisms, such as human immunodeficiency virus (HIV), hepatitis B virus (HBV) and hepatitis C virus (HCV) before, during or after glove use for medically intended purposes is an emerging public health problem of major proportions. The magnitude of the problem is enhanced by the fact that antibiotic-resistant strains of staph and strep are evolving rapidly, and there are currently no cures for HIV, HBV or HCV infections.

2. Description of the Prior Art

In the tradition inaugurated by William Halsted±100 years ago, operating rooms in health care settings customarily supply sterile gloves in pairs, packaged in envelopes containing inner sterile envelopes having a pouch for each glove. After careful handwashing, the operating room nurse uses the first inner envelope to put on the first pair without help from another person, as described below. Then, she opens more sterile inner envelopes, and helps gowned surgeon(s) put on their gloves after thorough scrubbing of their hands, including fingernails, before donning their surgical gowns. If the gloves touch anything apart from a carefully sterilized operating field, the wearer leaves the operating field; discards the gloves and gown; scrubs his/her hands again and, then, puts on a new sterile gown and pair of gloves with assistance before continuing to participate in the procedure. All the gloves are discarded carefully after completion of the operative procedure, and all the participants wash their hands again.

During the performance of minor surgical procedures in HCS, wherein a scrub nurse does not assist the operator(s) to put on sterile gloves, after careful handwashing, the operator is obliged to glove himself/herself without touching the external surfaces of either glove. Unassisted gloving is customarily performed by opening a sterile inner envelope, which folds open to expose two sterile surgical gloves in pouches. Each sterile glove is supplied with the fingers and palm outstretched, and a long cuff which is over-folded, such that the surgeon or a nurse can grasp the crease in the over-fold to manipulate each glove. A right-handed surgeon customarily uses fingers 1-2 of the left hand to grasp the crease of the glove for the right hand and, then, puts the right hand in without touching the external surface. Next, the surgeon grasps the crease of the glove for the left hand with fingers 1-2 of the left hand and, then, slides fingers 2-3-4 or 2-5 of the gloved right hand under the cuff over-fold, so that the left hand, after releasing the crease, can slide into the glove without touching the external surfaces. Finally, after the left hand is fully gloved with the over-fold extended to cover the wrist, the surgeon slides fingers 2-3-4 of the gloved left hand under the over-fold of the right glove to extend the cuff over the wrist of the right hand. Subsequently, bi-manual adjusting of each hand into each glove can be accomplished comfortably without external contamination of either glove. As combined results, the patient is protected before operation from any pathogenic microorganism commonly or conceivably carried by gloves or unwashed hands. If the surgeon gowns to perform a minor procedure, the glove cuffs extended over each wrist are designed to firmly and adequately grasp the wrist cuffs on his/her surgical gown.

By contrast, in remaining parts of health care settings, latex or synthetic gloves are currently supplied in closed unsterile boxes containing ±100. After the boxes are opened, the gloves without over-folded cuffs, or with short rolled cuffs, are extracted by grasping whatever part of the glove or parts of two gloves are randomly exposed through a slot in the box. Depending variably on what exposed part of the glove is grasped, the non-dominant hand is variably employed to glove the dominant hand. Subsequently, if a pair is put on, the dominant hand is employed to glove the non-dominant hand; again depending variably on what part of the empty glove was grasped. Often, users will pull two gloves from the box; stuff whatever protrudes from the box back in with an ungloved hand; and, then, proceed to glove both hands in accordance with what parts they have grasped and what works best for each user taking singles or pairs from a box holding ±100.

Thereafter, the gloves are worn for variable periods of time by HCW outside of sterile fields wherein any particle becoming adherent to latex can be rubbed off on a dry surface or eluted on a wet surface. Particulate rubbing off or elution becomes especially critical during the insertion of a hollow-bore steel needle into a vein, because needle users need to feel over, as well as see the vein before inserting the sharp bevel of the needle through the skin. As results, any microorganism, foreign particle or bloody fluid rubbed off or eluted is provided with immediate venous access and systemic circulation within 30 seconds. Most commonly in clinical laboratories where venous blood is withdrawn for testing, boxes of unsterile gloves are situated on shelves near the needles, syringes and tubes used for collecting blood from patients. Careful observation will reveal that the laboratory technicians called the phlebotomists, responsible for collecting blood, usually pull a pair from an open box, put them on, and proceed to pick up needles, special holders for needles and special vacuum tubes from separate unsterile containers and place them near an arm rest for the arm selected for phlebotomy. Both gloved hands are then used to put on a tourniquet for making a selected vein stand out. One gloved hand, usually the non-dominant hand, is then used to wipe antiseptic over the selected vein. After this, the dominant hand picks up an assembled needle attached to the special holder for the special vacuum tube. The gloved non-dominant hand is then used to take an unsterile protective scabbard off the sterile needle. Next, the non-dominant hand is used to feel over the vein and properly direct the thrust of the needle held in the dominant hand. Sometimes, but not always the forefinger of the non-dominant hand will actually feel over and touch the skin through which the needle must pass to withdraw venous blood. After the needle is properly placed inside the vein, the non-dominant hand is used to insert one or more vacuum tubes into the special holder for collecting specified samples. When sufficient blood is collected, the non-dominant hand is commonly used to remove the tourniquet from the patient's arm and then place a sterile pledget over the venipuncture site to hold pressure over the selected vein while the dominant hand withdraws the needle and disposes of the needle, the special holder and the vacuum tubes containing blood. Usually, the forefinger or thumb of the non-dominant hand will need to hold pressure over the venipuncture site at least 15–30 seconds to prevent bleeding, as well as injury to the vein. Meanwhile, the dominant hand, after disposing of the needle, special holder vacuum tube, is used to fetch a Band-Aid which is placed over the venipuncture site after the non-dominant hand becomes free to help. Finally, the phlebotomist takes off both gloves, and usually washes his/her hands.

The hazards involved become compounded if the needle user reuses the gloves or does not safely discard the needle/syringe and change gloves and handwash as soon as possible after the hollow needle is withdrawn. For instance—the finger or hand which was used to feel for the vein before inserting the hollow needle must be used for seconds or minutes after needle withdrawal to minimize venous bleeding from the patient. Because some venous blood leakage is unavoidable, the finger which holds pressure on the skin overlying venipuncture site can be contaminated with the patient's blood, even though a blood absorbent pledget is usually placed between a gloved finger and the skin. If the needle user uses the same glove on the next patient, the sharp bevel of the next sterile hollow needle is potentially contaminated with blood from the previous patient. As a result, the next patient is at risk for an intravenous injection of bloodborne, as well as skin-borne microorganisms of varying antibiotic sensitivity, as well as virulence.

Most gloves used within and outside of health care settings are supplied as examination gloves fitting either hand. They are not supplied sterile or in sterile boxes. From each box the user must extract single gloves or pairs by grasping the external surfaces of fingers, palms or short cuffs, as described. Therefore, the instant invention of packaging multiple sterile gloves with over-folded cuffs for examination or utility use in health care facilities, more or less like tissues from Kleenex boxes, appears novel.

With respect to right and left hand surgical gloves, each having the thumb apposed toward the palm, the sterile paper inner envelopes in current use open to expose a right and left pouch wherein the right and left glove are contained with the fingers exposed beyond the long cuff/palm overfold. Thus, it is possible for the user to bare-handedly grasp the fingers, instead of the crease of each cuff overfold to extract each glove from its own pouch. Moreover, because the creases are usually recessed in each pouch, the user is customarily obliged to touch the inside of the pouch to grasp each crease. Therefore, the instant invention appears novel because the container or package, when opened, presents only the crease and proximal part of the long cuff/palm overfold for manual grasping.

Alternatively, pairs of surgical gloves are supplied in boxes containing single envelopes. The boxes are not usually supplied with covers to keep the boxes sterile before being opened. The single envelopes are usually supplied with a peel-apart or rip-off means for opening the envelope on the end nearest the crease of the long cuff overfold. However, the crease and proximal part of the long cuff overfold are characteristically recessed in the envelope, such that the user is obliged to touch the inside of the opened package with bare fingers in order to grasp the crease and proximal part of the long cuff overfold. Thus, when the gloves are pulled out, the dorsal surfaces of the glove fingers can be expected to touch a potentially contaminated surface during extraction from the envelope. It will be noted that the instant invention attempts to eliminate this possibility by making the envelope actually open over the proximal part of the long cuff overfold.

Prior patents, possibly applicable to this invention include:

1. A glove dispenser—U.S. Pat. No. 5,088,620 (Feb. 18, 1992) by Kelliher and Schutt who described a tubular glove dispenser having an inside spring mechanism for pushing out a plurality of gloves, one at a time. Folding of the glove cuffs over the palms was not mentioned and the drawings show the gloves coming out fingers first.

2. A package dispenser for a plurality of surgical gloves—U.S. Pat. No. 5,456,345 (Oct. 10, 1995) wherein F Wood described a container holding multiple gloves packed inside one another, such that controlled vacuum in the container allows a surgeon to insert his hand and put on one glove at a time. Folding the glove cuffs over the palms was not described or claimed.

3. A sterile plastic glove and package assembly for packaging, putting on, and disposing of a glove was described by J Hummel in U.S. Pat. No. 3,870,150 (Mar. 11, 1975). This applies only to single gloves. Long cuffs, over-folding of cuffs, palms, fingers were not mentioned.

4. Two layer sterile packaging of gloves, along with other instruments was described by J Center in U.S. Pat. No. 3,926,309 (Dec. 16, 1975). The gist was packaging of gloves along with catheters in separate pouches. Overfolding of cuffs over palms was not described or claimed. However, overfolding of the cuffs is now common in the packaging of surgical kits containing a variety of items, all enclosed in the same pouch.

5. Currently, conventionally packaged sterile surgical gloves with overfolded cuffs list @ $ ±0.70/pr. or more depending on added features. Similarly packaged sterile examination gloves with overfolded cuffs list @ $0.50–0.75/pr. and 0.32 per single glove. Without interior wrapping, packaged single examination gloves with overfolded cuffs list @ $0.27. None of the packages, or contained inner envelopes open to expose only the crease and adjacent part of the overfold. Non-sterile examination gloves without overfolded cuffs list @ $0.06–0.10/glove; and are usually packaged in boxes of 100, as described previously. Non-sterile utility gloves latter are commonly packaged in varying numbers, each glove being mounted on a sheet of paper. Lacking overfolded cuffs, boxed examination and utility gloves can not be put on without touching external surfaces, even if the boxes were sterile.

SUMMARY OF THE INVENTION

In accordance with aseptic principles established by William Halsted for surgical glove use ±100 years ago, we describe convenient sterile glove dispensers for limiting the spread of blood- and skin-borne microbial infections from person-to-person in health care settings. The current, customary and widespread use of latex gloves apart from major and minor surgical procedures within health care settings makes it imperative to do so. Although the dispensers disclosed in a first embodiment specified herein can not preclude air-borne contamination of the enclosed gloves after removal of a sterile cover for each dispenser, airborne contamination can be minimized by appropriate construction, location, shielding and hanging of the dispensers. In a second embodiment pairs or single sterile gloves are dispensed in individual envelopes which open easily to expose only the creases of the long cuff over palm overfolds. The principal advantages of such dispensers are:

1. In sterile operating fields, such as in surgical operating rooms, after the outer envelope cover is removed to drop one or more sterile inner envelopes onto a sterile tray, the operating room nurse can glove herself with out assistance. Then, by opening successive sterile inner envelopes she can conveniently help glove or reglove multiple surgeons and nurses involved in the operation. This is especially advantageous because it allows the surgeon(s) to change gloves when they become sweat soaked, slippery or otherwise uncomfortable; and when operating in new fields opened by the same incision, such as splitting the sternum and, then, proceeding to do cardiac surgery requiring the placement of fine sutures deep in the chest; or proceeding with bowel reconstruction after draining an abscess. Exceptions are instances wherein a glove is accidentally and knowingly perforated by a sharp instrument. Then, it is necessary for the surgeon to drop out, unglove, handwash and reglove. If the perforation extended sufficiently through her/his skin to engender visible bleeding, the bleeding must be controlled before washing and regloving.

2. When a single surgeon is operating without assistance from an operating room nurse, the dispensers will allow surgeons to glove and reglove without breaking sterility of a limited field to open a new package containing a pair. Not one, but both gloves should be put on or changed as per the unassisted gloving procedure previously outlined.

3. Outside of sterile operating fields, the dispensers will permit users to perform procedures or manipulate objects, such that items touched with one or two gloved hands have not been contaminated by exposure to any thing tangible. For examples:

a. In health care settings, the use of a single glove fresh from a box dispenser on the non-dominant hand used to feel over a vein during the performance of a venipuncture might prevent contamination of a patient's blood stream.

b. The use of a single sterile glove on the dominant hand might be desirable when doing a pelvic examination, touching inflamed skin or mucus membranes, or touching potentially contaminated body secretions. Immediately following such usages, the opposite hand should remove the glove by grasping the cuff to take off and discard the glove such that it cannot be used to touch another person. Immediately after, both hands should be washed.

c. In dental care settings, where the dentist or dental assistant is obliged to work inside the mouth, such sterile glove dispensers could significantly decrease the rate of post-treatment infections for the following reasons:

i. Dental office surveys by means of hidden video cameras reveal that sampled dentists wash their their hands before donning gloves in only 23% of patient contacts; and change gloves between patients in only 56% of contacts [Cf. Porter et al. *British Medical Journal* 1996; 312: 705].

ii. If the wash-basins and glove dispensers are properly placed in dental treatment rooms, clients can easily see if the dentist or dental assistant washes his/her hands and puts the gloves on without contaminating the external surfaces before starting and between oral procedures.

4. Such box dispensers can be supplied loaded with more than one externally sterile glove, such that given numbers for the right hand, left hand, either, or both can be supplied in accordance with intended usages.

5. As opposed to examination or gloves supplied in unsterile boxes containing ±100, sterile gloves with over-folded cuffs, when supplied in dispensers containing pre-selected numbers of the highest available quality and adapted to customary hand use, can prove very cost effective in terms of optimal patient care.

6. Whether or not the dental or surgical glove user washes her/his hands adequately before and after glove use, a conscious patient will be able to discern or, at least ask, what the gloves have, or have not, touched before their intended use.

7. Finally, the magnitude of the unsterile glove problem comes into focus when one considers:

a. Apart from designated surgical operating rooms, unsterile examination gloves are currently being used at the rate of more than 10 billion/yr. in U.S. health care facilities.

b. Studies by trained observers in sampled intensive care units and emergency rooms reveal that health care workers wash their hands before and after each patient contact only 20–40% of the time [Cf. Wurtz et al. *Am J Infect Control* 1994; 22: 228–230; Nystrom. *Infect Control Hosp Epidemiol* 1994; 15; 435–436; Meengs et al. *J Emerg Nurs* 1994; 20: 183–188].

c. A recent survey in a long-term health facility found that health care workers washed their hands before putting on examinations gloves, only 27 times out of a hundred. [Cf. Thompson B L et al *Infect Control Hosp Epidemiol* 1997; 18: 97–103.]

d. The increased use of latex gloves by health care workers to protect themselves from HIV and HBV infections has led to a false sense of security among health care workers and patients; and has lead to wide-spread failure to wash hands properly and adequately during patient care [Cf. Heptonstall & Mortimer. *Lancet* 1995; 345: 599–600].

Thus, the supply and use of the box and/or envelope embodiments of overfolded sterile glove dispensers disclosed herein could prove to be significant advance in public health at a reasonable; and an advance which can be monitored by patients, as well as health care workers.

BRIEF DESCRIPTION OF DRAWINGS

FIG. 1 is a diagrammatic side view of touching dispenser containers for right and left hand surgical gloves with thumbs apposed toward the palms and long over-folded cuffs, showing serial folding of glove cuffs over fingers inside each container and exposed creases of the over-folded cuffs protruding from slits in each container below.

FIG. 2 is a perspective view of the first and second fingers of the left hand grasping the crease of a cuff overfold extracted from the right hand container in order to glove the right hand without touching the external surface of the right glove.

DESCRIPTION OF PREFERRED EMBODIMENTS

Figure 3:
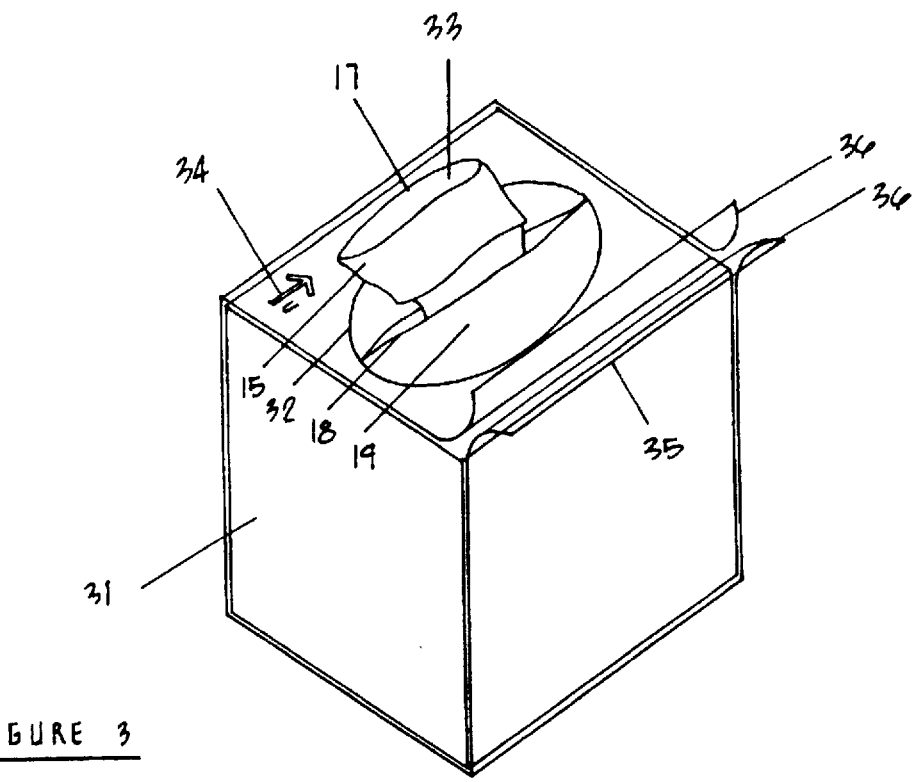
FIG. 3 is a perspective over-view of a dispenser for right, left or either hand gloves, showing a slit through which each glove with a long over-folded cuff is manually extracted via a film-covered ovoid slot in each dispenser supplied with an easily removed sterile cover.

FIG. 1 shows side-by-side dispensers (11,12) for multiple left (13) and right (14) hand surgical gloves, respectively.

Inside each container long over-folded cuffs (15) are serially folded over the glove fingers (16), such that pulling out each over-folded cuff by grasping the crease (17) in overfold causes the Fingers (16) of each glove to pull out the over-folded cuff (15) of the next via a slit (18) located in a plastic-covered slot (19) on the underside side of each container (11,12).

FIG. 2 shows the first and second fingers of the left hand (21) grasping the crease (17) on the palmar side of the cuff over-fold (15) of a right handed surgical glove (14) having the receptacle (22) for the right thumb (23) apposed toward the fingers (16) and palm of the glove (14). The right hand (24) slides into the glove as the left hand (21) pulls back on the crease (17).

FIG. 3 shows a dispenser (31) having an ovoid slot (32) covered by a plastic material (19) with a slit (18) through which the long over-folded cuff (15) of a utility glove (33) is exposed and, later, extracted as shown in FIG. 2. An arrow (34) on the side of the container through which the glove (33) is extracted by grasping the crease (17) indicates the orientation of the thumb of each glove inside the dispenser (31). A marker (U) L, R, or U is situated beside the arrow to indicate whether the container holds left, right or utility gloves. The dispenser (11,12,31) is supplied enclosed within an air-tight cover (35) which is removed by spreading apart paired sealing tabs (36) such that the container can be dropped out onto a sterile surface or a clean surface without touching or being touched by any other object. It is important to note that the first glove in each sterile-covered container, whether for left hand surgical gloves, right hand surgical gloves or for utility gloves fitting either hand, extrudes through the slit (18) such that the long folded-over cuff (15) is accessible for grasping over the crease (17), as shown in FIGS. 1 and 3. This is essential for three reasons:

a. Exposure of the crease (17) through the slit (18) allows an ungloved user to grasp the over-folded cuff (15) of the first glove without contaminating the box (11,12,31) or the external surface of any contained glove.

b. The length of the slit (18) or slits in the ovoid plastic-covered slot (19) is critical to minimize contamination of the container by air-borne particles.

c. The length of the slit (18) in relation to the ovoid plastic-covered slot (19) is critical to the combined splaying of the slit (18) or slits (not shown) and outward bending of the plastic film material (19) when the fingers (16) of the serially over-folded gloves pull out the cuffs (15) of each glove successively retrieved from the container.

Thus, in contrast with a box of tissues, such as Kleenex™, or a container holding ±100 latex examination gloves, the user does not pry open the slit or open the slot with a finger to access the first glove and each glove extracted thereafter.

Figure 4:
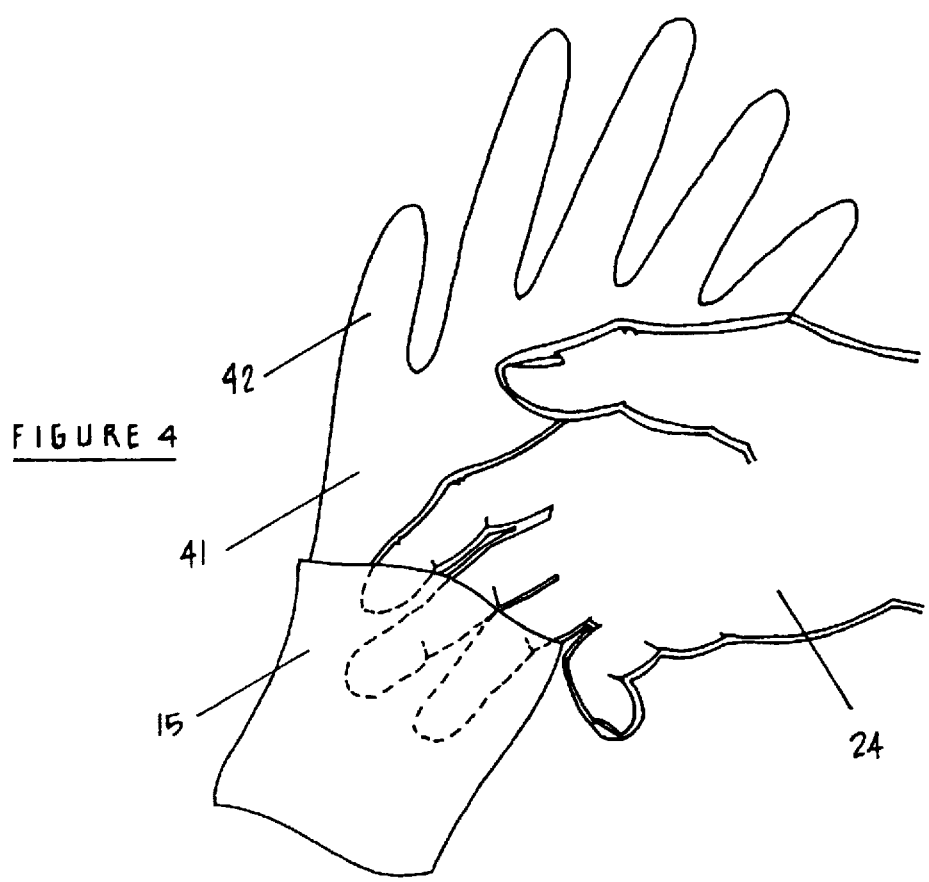
FIG. 4 is a perspective view of a utility glove, without an apposed thumb, showing how after extraction of the glove through the slit in the container by means of the first and second fingers of an ungloved hand (as shown in FIG. 2), the second to fourth or fifth fingers of the gloved hand use the underside of the long glove overfold to glove this hand.

FIG. 4 shows an examination glove (41) lacking an apposed thumb (42) and having the thumb upward in the position it would normally reside after retrieval of the glove (33,41) from the container (31) of FIG. 3 by grasping the crease in the the dorsal side of the glove over-fold (15) with the first and second fingers of the left hand (not shown). The sterile gloved second, third and fourth fingers of the right hand (24) are shown underneath the glove overfold in proper position for helping to insert the left hand into this examination glove (41) without contaminating the external surface.

In surgical settings, such as operating rooms where several nurses and surgeons are participating in a surgical procedure, sterile-covered containers each holding 6–12 sterile right and left surgical gloves with apposed thumbs could be supplied separately, or with containers for left and right gloves placed side-by-side, as shown in FIG. 1. The operating room nurse responsible for gloving herself and other participants should have an assistant with clean hands take the cover (35) off the container, such that the container drops untouched onto a sterile flat surface in the sterile operating field, preferably with the slit exposed such that she can directly grasp the crease in the overfold of the first glove in each container. After gloving herself, she can safely manipulate each container or pair of containers to help glove or re-glove the remaining participants. It will be found that, after retrieving the first 2–3 gloves in each container, smoothest procedure for retrieval of the remaining gloves will occur if the slits face downward, such that the force of gravity presses each remaining glove toward the slit. If more containers of left, right or pairs of surgical gloves are needed, the responsible operating room nurse can direct an assistant apart from the sterile operating field to drop in more without touching the external surfaces of the containers or the exposed cuffs on the gloves. The opened containers, then, can be placed on a suitable rack with their openings facing down.

On the other hand, in medical settings such as examining rooms, treatment rooms or laboratories, where single or pairs of sterile examination gloves fitting either hand are used for a given procedure, sterile covered containers holding 12–24 or 48 gloves without apposed thumbs would seem most efficient. The sequential users should be thoroughly familiar with sterile gloving technique for putting on one or two gloves, as shown in FIGS. 2,4. Also, users who are left-handed or ambidextrous should recall that the dominant hand should be gloved first, when putting on pairs. After removal of the covers which keep the boxes sterile, it would seem most efficient to hang the boxes with the slits downward in stable holders above eye level, such that the containers sequentially deliver all the gloves smoothly and contamination of the slits and box interiors by air-borne particles is minimal.

Figure 5:
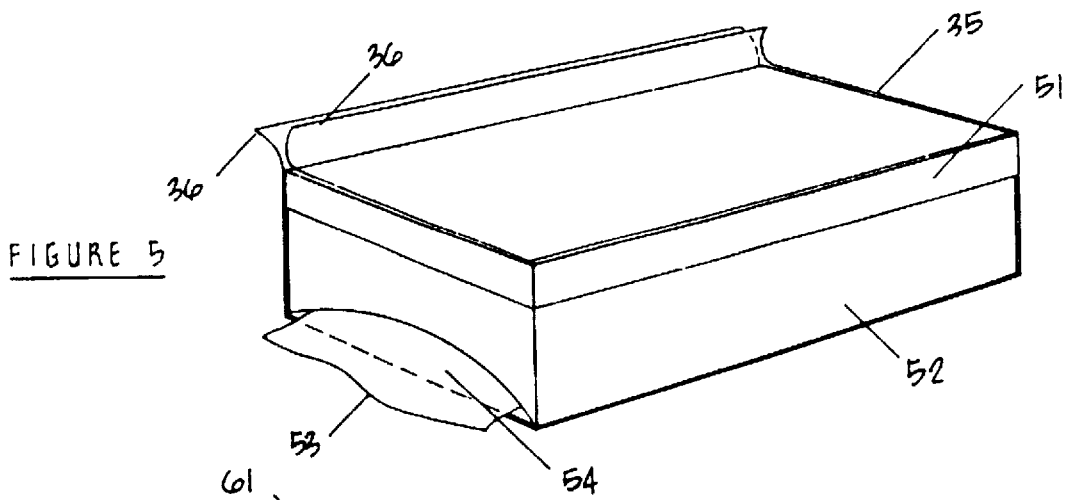
FIG. 5 is a perspective side view of a sterile container for dispensing single gloves or multiple pairs of gloves within easily-removed individual envelopes which strip or tear open to expose only the long cuff overfolds on each glove.
Figure 6:
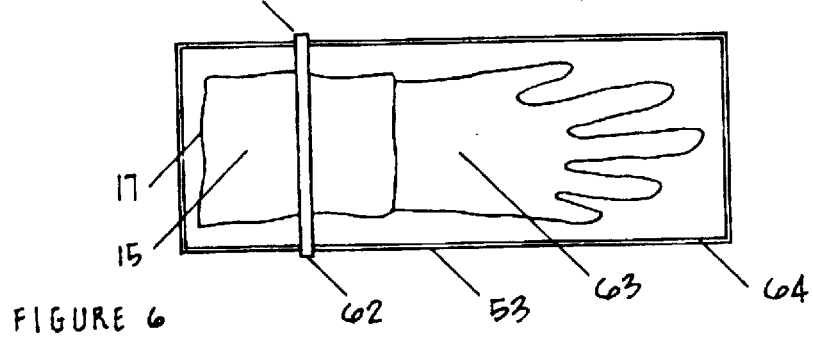
FIG. 6 is an over-view of an individual envelope with a stripping tab or tearing line for exposing only the crease and part of the overfold of each glove.
Figure 7:
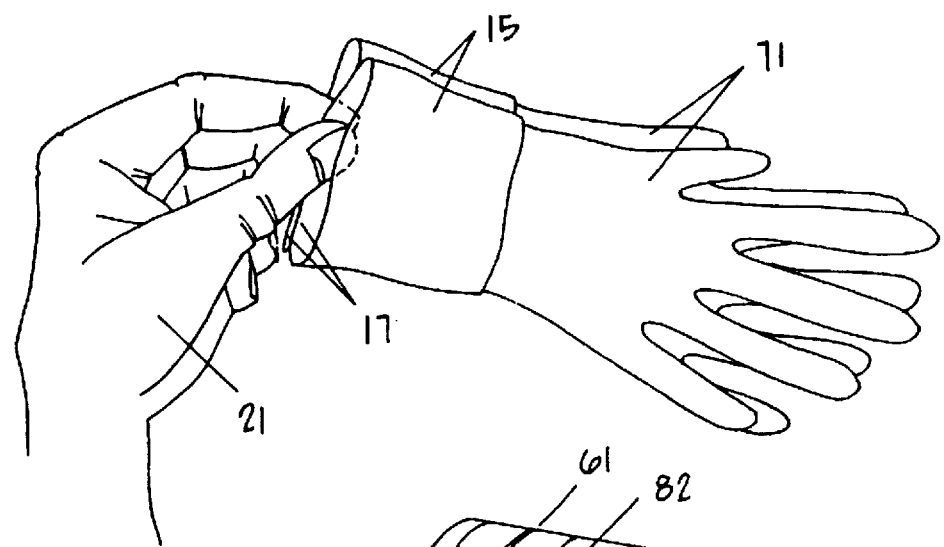
FIG. 7 is perspective view of the first and second fingers of the non-dominant hand grasping the creases of a pair of gloves, such that after removal from the envelope, each glove can be put on without contaminating the other.

FIGS. 5–7 show an alternative embodiment of a dispenser for individually packaged sterile single or pairs gloves with long cuff over-folds. FIG. 1 shows an easily removed air-tight film cover (35) with spreading tabs (36) completely enclosing a container having a cover (51) which slides over the container (52) holding individual envelope-like packages (53) of sterile gloves. The leading end of the container (52) is cut away (54) to expose the trailing ends of the individual glove envelopes (53) after the film cover (35) is removed.

FIG. 6 shows the individual glove envelope (53) after manual removal from the container shown in FIG. 5. The envelope (53) made from air-tight paper or plastic to form a sealed envelope has a stripping mechanism (61-62) wherein pulling a tab or tearing from (61) to (62) removes the entire end of the envelope to expose the creases (17) and trailing part of the over-folds (15) of the contained sterile gloves (63). It is important to note that the entire perimeter of the envelope-like package is sealed (64) by folding over, or adhesion between layers.

FIG. 7 shows the first and second fingers of the left hand (21) grasping the creases (17) of a pair (71) of sterile gloves after their manual removal from the individual envelope (53), such that neither external glove surface is touched or touches another object before the pair of gloves is put on as shown in FIGS. 2 and 4.

Figure 8:
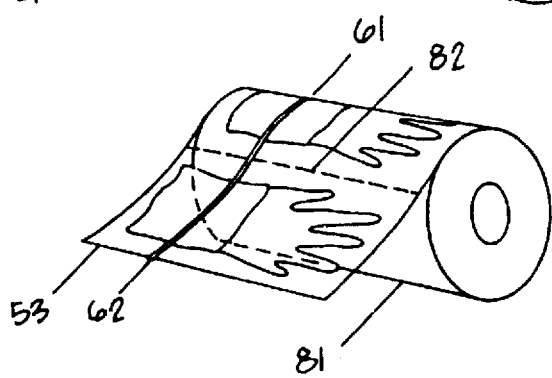
FIG. 8 shows individual envelopes supplied in rolls.

FIG. 8 shows multiple envelope-like packages (53) dispensed in rolls (81), instead of boxes. Perforations (82)

through the adhesive seals between successive envelopes allow the user to rip off glove containing envelopes one at a time and grasp the gloves after removing the end of each envelope, as outlined above. This alternative for dispensing gloves contained in sterile envelopes might prove very convenient outside of surgical settings.

Normally a right-handed person grasps the creases of both gloves with the left hand to hold a pair, gloves the right hand as shown in FIG. 2 and, then, releases the crease of the right hand glove, such that the second to fourth or fifth fingers of the right hand can slide back under the over-fold of the left hand glove to glove the left hand. When the right hand has gained control under the overfold of left glove, the first and second fingers of the left hand let go of the crease. Finally, when both hands are gloved without touching the external surfaces, both hands adjust the gloves such that each fits and feels comfortable.

This alternative dispenser embodiment shown in FIGS. 5–8 is equally applicable to single gloves, pairs of surgical gloves having apposed thumbs and pairs of examination gloves without apposed thumbs. This embodiment might be especially applicable for dispensing single gloves with special adaptations, such as reinforcing the strength and thickness of the glove covering the index finger of the non-dominant hand. Because the user can see the position of the glove thumb or thumbs and little fingers through plastic film-like material, the dispensers need not be marked for indicating the position of the glove thumb. The dispenser box and the individual glove packages should be marked to indicate the kind of glove, size, number contained and where to be grasped by left-handed, as well as right-handed users. The individual glove packages should stay in the sterile dispenser boxes or rolls until just before the gloves are extracted for surgical use or medical use.

Finally, it should be noted that surgical and utility gloves are fabricated with cuffs of varying length relative to the palms and fingers. Surgical gloves characteristically have relatively long cuffs whose proximal ends are scalloped or rolled tightly to enhance grasping by fingers or adherence over surgical gowns. Examination gloves usually have relatively short cuffs, often with tightly rolled "beaded" proximal ends to enhance finger grasping. Nevertheless, it is important that the length of the cuff over palm overfold is long enough to prevent touching of the palms or fingers when the crease of the overfold is grasped to glove one or both hands.

Minor details not illustrated:

1. In the box dispenser version for multiple envelopes containing sterile gloves shown in FIG. 5 with a peel opener (36-36) for taking the air-tight film cover (35) off the box (52), it might prove more convenient to use a tab type stripper, like that normally used to open a package of cigarettes, such that one end of the film cover can be stripped off entirely to deliver the box untouched into a sterile operating field by grasping the opposite end of the film cover and shaking the box out with the help of gravity.

2. In the roll dispenser (81) version for peeling off multiple envelopes containing sterile gloves shown in FIG. 8, it might be preferable to use a tear off version for opening each envelope (53), as well as ripping successive envelopes from the roll. In this case, the perforations (82) should made such that the line of shearing each envelope from the roll puts minimal stress on the line of opening each envelope (61-62). Alternatively, the perforations could be spaced such that shearing of the envelope from the roll and and opening each envelope could be made in one motion wherein the direction of force applied changes from horizontal at a preselected point. The former is probably more fool-proof.

3. Preferably, the roll dispenser (81) version should be packaged in sterile boxes with air-tight film covers as shown in FIG. 5, such that the rolls can be dumped directly into sterile operating fields and such that each roll is shielded during storage and distribution.

4. An added consideration is that the envelope-containing boxes (52) shown in FIG. 5 can be fabricated such that the lower aperture (54) is omitted and the upper cover (51) is modified to hinge open. As results rolls of sterile glove containing envelopes can be extracted from the box, more or less like saran-wrap or aluminum foil is extracted from a roll in a box. However, owing to the fact that roll (81) is made with perforations (82), a sharp saw-like edge on the box cover (51) would be inappropriate.

5. It should be obvious to frequent users of sterile gloves that one gloved hand is often sufficient for multiple individual purposes, such as performing a pelvic examination, a rectal examination, feeling inside the mouth, feeling over an abscess for finding the best place to incise, feeling over inflamed skin or mucus membranes to identify an underlying abscess or tumor, or just feeling over abnormal appearing areas of skin or membranes to assess the underlying pathology. It should be equally obvious to those familiar with the manufacture and packaging of gloves that a single sterile glove, enveloped such that the user can first grasp a tightly rolled beaded crease on the proximal portion of a standard examination glove cuff, instead of the crease inherent in a long cuff/palm overfold, to glove a single hand without the beaded-crease-grasping hand touching anything beyond the beaded cuff. Thus, a single sterile glove, packaged as previously described in a dispensing box capable of consecutively delivering 100 with only the beads exposed for finger-grasping, or in separate boxed or rolled envelopes whose manual opening exposes only the proximal beads for ready finger access without contaminating the leading parts of the gloves, would seem ideal in terms of preventing user to patient and patient to user cross-infection with diverse blood- and skin-borne microorganisms nobody wants to have shown in FIG. 4. Thus, for sterile gloving one or both hands, a long overfolded cuff is necessary. However, for sterile gloving a single hand, the use of a trailing bead which allows the user to firmly grasp the proximal part of the glove securely can be expected to work equally well when only one glove is needed to prevent user to patient and patient to user cross-infection with blood- or skin-borne microorganisms nobody wants to have 6. Standard gamma radiation in FDA- approved facilities should be used to sterilize all glove dispensers and their contents disclosed above.

The foregoing specifications are exemplary and designed to be convenient, efficient and cost-effective for packaging sterile surgical and examination gloves commonly used in astronomic numbers in health care settings. Those familiar with the art of packaging and maintenance of sterility might envision other useful versions. However, the crux of this invention lies in exposing only the crease of the cuff over palm fold or a proximal part of a beaded glove for finger grasping, such that the user does not put fingers inside a box, package or an envelope to extract the gloves, before putting the gloves on by time-honored techniques for unassisted gloving with two or one sterile gloves.

Therefore, we claim:

1. A dispenser for sterile medical gloves, each having a fitting thumb, four fingers, a palm and a cuff folding outside over the palm and dorsum of each glove to form a cuff overfold for finger grasping, the dispenser comprising a box wherein:

(a) a plurality of gloves are folded serially over one another with the cuff of each glove overlying the fingers of the next, such that grasping the cuff overfold for glove extraction will cause the fingers of each glove to pull out the cuff of the next glove until said box is emptied, more less like a box of Kleenex tissues;

(b) the cuff overfold of the first glove protrudes through a permanent opening in said box, such that grasping fingers are never inserted through said opening to extract the first, second or any subsequent glove to be extracted, and such that fingers grasping the cuff overfold do not touch the thumbs, fingers or palm of any glove during the process of extraction;

(c) said opening in said box is covered by a slit membrane which allows each glove to pass through, but limits access of airborne particles to the sterile gloves inside said box;

(d) the thumb of each folded glove is located in one side of the box externally labeled right or left to accommodate the handedness of the glove user;

(e) optional means are provided for hanging said box in an inverted position such that said opening is dependent for preventing contamination by airborne particles and such that the force of gravity will cause each successive glove to fall toward said opening until said box is emptied; and (f) whereover an easily removed sealing cover is provided to keep said box and its contents sterile until dispensed into a sterile operating field, or until said sealing cover is removed for use of the contained sterile gloves elsewhere.

2. A dispenser, as in claim 1, alternatively comprising a sealed sterile envelope containing one sterile glove or a pair of apposed sterile gloves and wherein (a) the thumb, fingers, palm and cuff of each glove in a pair are apposed touching one another, such that opening said sealed sterile envelope by complete tearing across both sides on the end containing apposed cuffs will immediately and directly expose the cuff overfolds of both gloves for grasping with one hand, so that each glove can be donned by standard unassisted technique without a bare finger or hand touching the external surfaces of the thumb, fingers, palm or dorsum of either glove, without touching the internal surfaces of said sealed sterile envelope, and without touching the external surfaces of said sealed sterile envelope with any glove part during or after the extraction of one or both gloves; and (b) whereover an easily opened, sealed, inside sterile container is provided to contain a plurality of said sealed sterile envelopes containing single gloves or pairs of said apposed sterile gloves, such that given numbers can be dispensed sterile for surgical or medical use.

3. A dispenser, as in claim 2, further comprising a roll of said sealed sterile envelopes containing a single sterile glove, or a pair of apposed sterile gloves and wherein:

(a) each sealed sterile envelope is releasably attached to the next along the long sides of the envelopes such that, after detachment, the short ends of said sealed sterile envelopes overlying the glove cuffs can be completely torn open more or less at right angles to the long axes of said sealed sterile envelopes and the contained gloves to expose the cuff overfolds for finger grasping; and (b) whereover an easily removable sterile sealing cover is provided to keep said roll and its contents sterile and protected until dispensed into a sterile operating field, or until said sealing cover is removed for use of the contained sterile gloves in other health care settings.

* * * * *